United States Patent [19]
Alvarez

[11] 3,960,957
[45] June 1, 1976

[54] 2-(6'-METHOXYNAPHTH-2'YL) PROPIONALDOXIME AND 5'-HALO DERIVATIVES THEREOF

[75] Inventor: Francisco Sánchez Alvarez, Sunnyvale, Calif.

[73] Assignee: Syntex Corporation, Panama, Panama

[22] Filed: Jan. 10, 1975

[21] Appl. No.: 540,011

Related U.S. Application Data

[62] Division of Ser. No. 354,537, April 26, 1973, Pat. No. 3,873,594, which is a division of Ser. No. 151,921, June 10, 1971, Pat. No. 3,758,544, which is a division of Ser. No. 748,603, July 30, 1968, Pat. No. 3,637,767.

[52] U.S. Cl................................... 260/566 A
[51] Int. Cl.$^2$...................................... C07C 131/00
[58] Field of Search................................ 260/566 A

[56] References Cited
OTHER PUBLICATIONS

Chemical Abstracts, vol. 17, p. 102 (1923).
Chemical Abstracts, vol. 40, column 3429$^7$ (1946).
Chemical Abstracts, vol. 40, column 1045(f) (1952).

Primary Examiner—Gerald A. Schwartz
Attorney, Agent, or Firm—Joseph I. Hirsch; William B. Walker

[57] ABSTRACT

New compounds, 2-(6'-methoxynaphth-2'-yl)propylene oxide, 2-(6'-methoxynaphth-2'-yl)propionaldoxime, 2-hydroxy-2-(6'-methoxynaphth-2'-yl)-propionitrile, 2-(6'methoxynaphth-2'-yl)acrylonitrile, 2-(6'-methoxynaphth-2'-yl)acrylic acid, the corresponding 5'-halo compounds and 2-(5'-halo-6'-methoxynaphth-2'-yl)propionaldehyde are useful intermediates in producing 2-(6'-methoxynaphth-2'-yl)propionic acid and the corresponding 5'-halo acids from 6-methoxy-2-acetylnaphthalene and the corresponding 5-halo compounds. The 2-propionic acids are anti-inflammatory, analgesic, anti-pyretic and anti-pruritic agents. The 2-propionaldehydes, obtained from the 2-acetyl compounds by way of the 2-propylene oxide, can be converted directly to the 2-propionic acids by way of the 2-propionaldoximes and the 2-propionitriles or more directly by Jones oxidation. Alternatively the 2-acrylonitriles, obtained from the 2-acetyl compounds by way of the 2-hydroxy-2-propionitrile, can be converted to the 2-propionic acid by way of the 2-acrylic acid or 2-propionitrile.

1 Claim, No Drawings

2-(6'-METHOXYNAPHTH-2'YL) PROPIONALDOXIME AND 5'-HALO DERIVATIVES THEREOF

This is a division of application Ser. No. 354,537, filed Apr. 26, 1973, now U.S. Pat. No. 3,873,594, which is a division of application Ser. No. 151,921, filed June 10, 1971, now U.S. Pat. No. 3,758,544, which in turn is a division of application Ser. No. 748,603, filed July 30, 1968, now U.S. Pat. No. 3,637,767.

It is the object of this invention to provide new compounds and processes for making them, which compounds are useful as intermediates in improved methods for producing 2-(6'-methoxynaphth-2'-yl)propionic acid and the corresponding 5'-halo propionic acids.

The compounds, 2-(6'-methoxynaphth-2'-yl)propionic acid and 2-(5'-halo-6'-methoxynaphth-2'-yl)propionic acid and the novel intermediates therefor of the present invention can be prepared by processes exemplified as follows, wherein X is halo (fluoro, chloro, bromo or iodo) and Y is hydrogen or X:

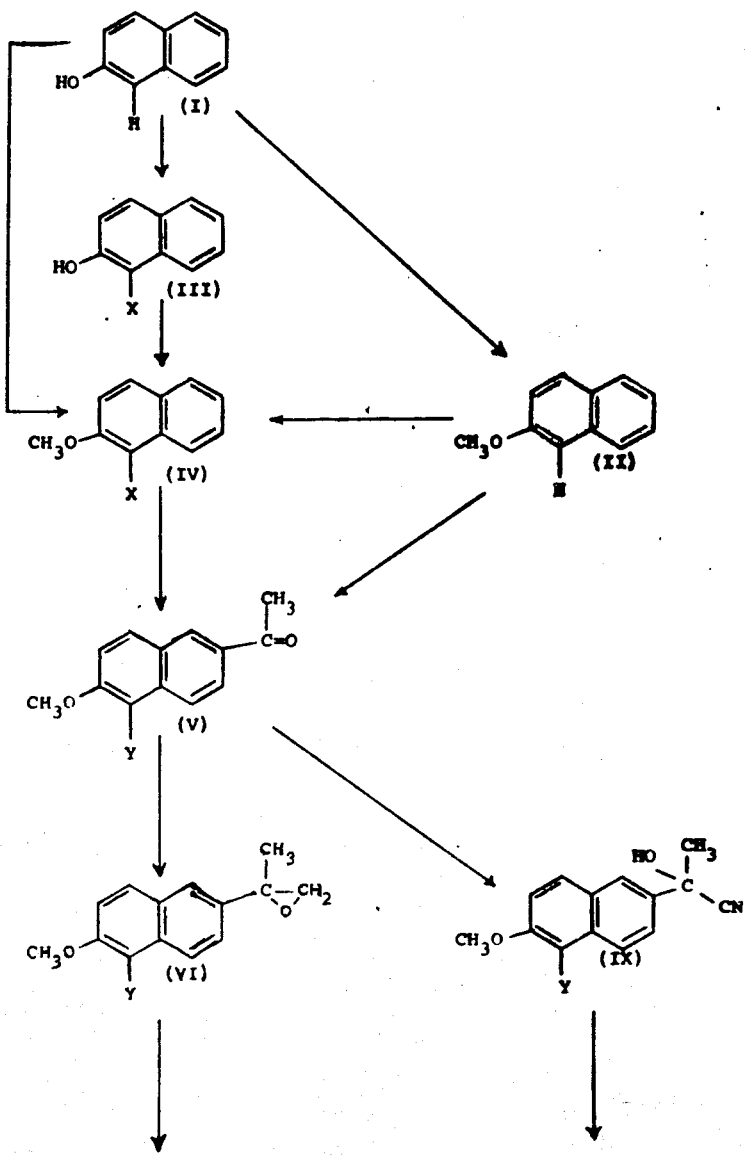

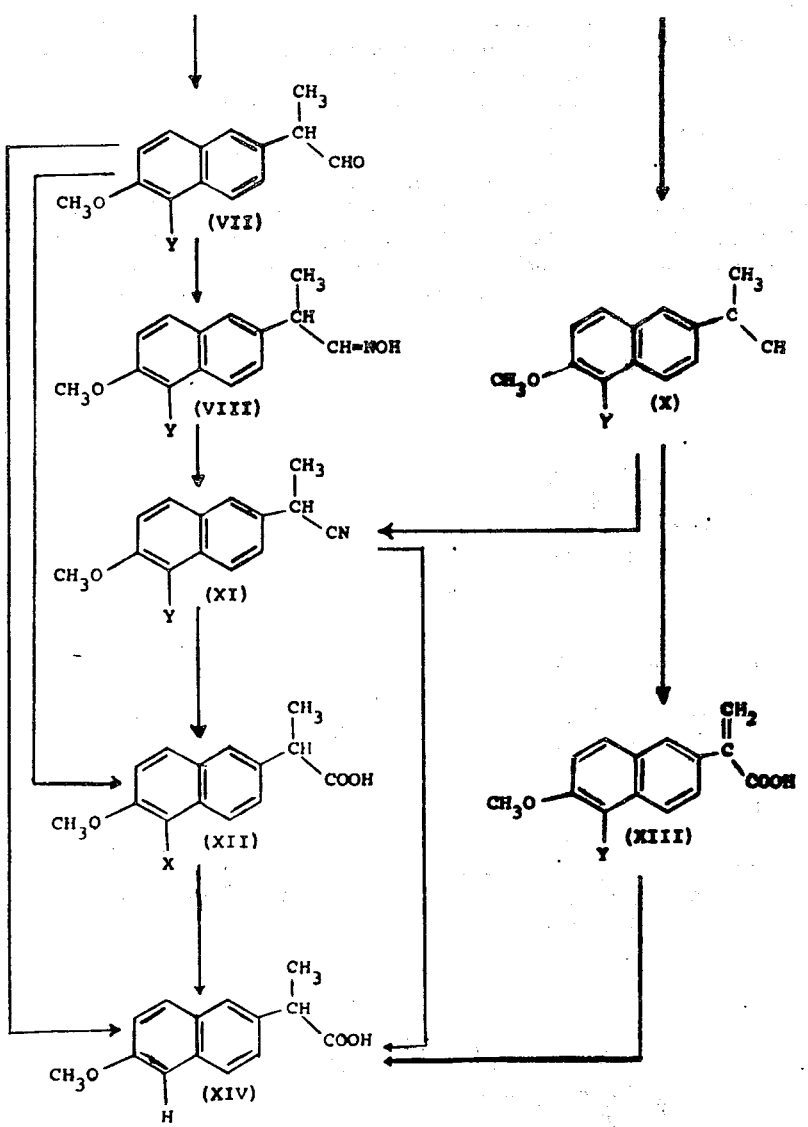

The 2-(6'-methoxynaphth-2'-yl)propionic acid and corresponding 5'-halo compounds are useful as an anti-inflammatory, analgesic, anti-pyretic and anti-pruritic agents as described in U.S. application Ser. No. 694,771 filed Dec. 7, 1967. The acids can be used in the same manner as aspirin and phenyl butazone.

The preferred manner of oral administration provides the use of a convenient daily dosage regimen which can be adjusted according to the degree of affliction. Generally, a daily dose of from 0.1 mg. to 20 mg. of the active compound per kilogram of body weight is employed. Most conditions respond to treatment comprising a dosage level in the order of 1 mg. to 5 mg. per kilogram of body weight per day. For such oral administration, a pharmaceutically acceptable non-toxic composition is formed by the incorporation of any of the normally employed excipients. These compositions take the form of solutions, suspensions, tablets, pills, capsules, powders, sustained release formulations, and the like.

Referring to the above diagram, the intermediate and final products of this invention can be derived from the commonly known 2-hydroxynaphthalene ($\beta$-naphthol) of Formula I.

By contacting the 2-hydroxynaphthalene of Formula I with methanol in the presence of concentrated sulfuric acid at reflux temperatures, for example, 2-methoxynaphthalene is formed. This ether can be separated from the methanol layer of the reaction mixture by conventional means to yield 2-methoxynaphthalene, a known compound.

The 2-methoxynaphthalene of Formula II or 2-hydroxynaphthalene of Formula I is halogenated to introduce a halo group (iodo, bromo, chloro or fluoro) preferably a fluoro, bromo or chloro group at the C-1 position of the naphthalene nucleus. The substitution reaction can be carried out by any conventional technique suitable for the naphthalene system. For example, substitution with iodine, bromine or chlorine can be effected by the procedure described in Ber. 21, 891 (1888). Fluorination can be accomplished by the procedure described in J. Org. Chem. 33, 2469 (1968)

replacing estrone with equivalent amounts of 2-hydroxynaphthalene (Formula I).

Preferably, iodation, bromination or chlorination is effected with the halogen in an inert organic solvent, reacting the naphthalene compounds with a molecular equivalent of the halogen at temperatures which provide an efficient, effective reaction. Preferably the reaction is conducted in the presence of a suitable catalyst, although selective halogenation at the C-1 position proceeds very well without a catalyst. Suitable organic solvents include substituted aromatics such as nitrobenzene and halogenated aromatics including monochlorobenzene, the dichlorobenzenes, etc.; aliphatic liquid hydrocarbons having at least 8 carbons, chlorinated aliphatic hydrocarbons such as methylene chloride, tetrachloroethylene, carbon tetrachloride, pentachloroethylene, etc.; lower alcohols such as ethanol, butanol, etc.; ethers having up to 6 carbons such as diethyl ether; and lower aliphatic carboxylic acid such as acetic acid, formic acid and the like. The preferred solvents are carboxylic acids such as acetic acid or halogenated liquid hydrocarbons such as methylene chloride, monochlorobenzene, and the like. The elemental halogen is added directly or as a solution with one of the liquid components of the system. The catalysts which promote this reaction are conventional and well known in the art. Increased yields are often obtained if the reaction is conducted in the presence of lower aliphatic carboxylic acids such as formic acid, acetic acid, and the like. The presence of a small quantity of elemental iodine has been found to assist in initiating the reaction with bromine and chlorine. Iron salts such as ferric chloride also promote the reaction and increase the yield of the α-halo products.

The compounds of Formula IV (wherein X is an iodo, bromo or chloro group) can, alternatively, be produced by first halogenating the 2-hydroxynaphthalene and then forming the methoxy group. The halogenation can be carried out as described above to introduce halo groups, preferably a fluoro, chloro or bromo group at the 1-position of the naphthalene nucleus, yielding the 1-halo-2-hydroxynaphthalene of Formula III.

The 2-hydroxy compound of Formula III is then methylated with dimethyl sulfate in dilute alkali, for example, to form the 1-halo-2-methoxynaphthalene of Formula IV.

Of these alternative routes from the compound of Formula I to the compound of Formula IV, the preferred sequence of steps is a first methylation of the 2-hydroxy group followed by halogenation, since this permits the use of simple and more efficient reactions and less expensive reactants.

Fluorination can be accomplished by nitrating 2-hydroxynaphthalene (Formula I) with one equivalent of nitric acid in an inert organic solvent, to form 1-nitro-2-hydroxynaphthalene, reacting this with dimethyl sulfate in dilute alkali to form 1-nitro-2-methoxynaphthalene, hydrogenating the methyl ether over Raney nickel, for example, to form 1-amino-2-methoxynaphthalene, diazotizing this in aqueous fluoroboric acid to yield the 1-diazonium fluoroborate, and thermally decomposing the latter in the presence of copper powder to yield 1-fluoro-2-methoxynaphthalene (Formula IV).

The 6-methoxy-2-acetylnaphthalene and corresponding 5-halo compounds of Formula V are formed from the 2-methoxynaphthalene of Formula II or 1-halo-2-methoxynaphthalene of Formula IV with acetyl chloride or acetic anhydride by a Friedel-Crafts reaction in an inert organic solvent.

When the 2-methoxynaphthalene of Formula II is used as the starting material, the choice of solvent is very important to preferentially form the 6-methoxy-2-acetylnaphthalene. Conducting the reaction in a nitrobenzene solvent system has been found satisfactory. However, nitrobenzene is an expensive solvent, and the yields obtained with it are considerably lower than can be obtained by procedures operable with 1-halo-2-methoxynaphthalene starting materials. Separation of the product intermediate from the nitrobenzene is also somewhat difficult.

Therefore, the 1-halo-2-methoxynaphthalene of Formula IV is the preferred starting material since high yields of the corresponding 5-halo-6-methoxy-2-acetylnaphthylene compound of Formula V is obtained in conventional inert organic solvents without the need of a special solvent such as nitrobenzene. In the latter reaction, suitable inert organic solvents include chlorinated aliphatic hydrocarbons such as dichloroethylene, methylene chloride, carbon tetrachloride, chloroform, tetrachloroethylene, and the like.

The preferred catalyst is aluminum trichloride although other Friedel-Crafts catalysts such as Lewis acids can be used. Examples of suitable catalysts are ferric chloride, stannic chloride, boron trichloride, zinc chloride, zirconium chloride, hydrogen fluoride, concentrated sulfuric acid (96%), phosphorous pentoxide, phosphoric acid, and the like. The reaction is conducted at temperatures of from 0°–100°C and, depending upon the temperature, requires up to 10 hours for completion. With an aluminum trichloride catalyst, the reaction is preferably conducted at 0° to 30°C for from ½ to 2 hours.

After the product is formed in the reaction mixtures of both of the above processes, the organic layer containing the product is washed, concentrated, and the 6-methoxy-2-acetylnaphthalene or its 5-halo counterpart is crystallized, washed, recrystallized, washed and dried to provide the acetyl compound of Formula V wherein Y is hydrogen or halogen, depending upon its precursor.

In the above process, 6-methoxy-2-acetylnaphthalene or 5-halo-6-methoxy-2-acetylnaphthalene (Formula V) is reacted with dimethylsulfonium methylide or dimethyloxosulfonium methylide in an inert solvent to form the respective 2-(6'-methoxynaphth-2'-yl)propylene oxide or 2-(5'-halo-6'-methoxynaphth-2'-yl)propylene oxide in Formula VI. The dimethylsulfonium or dimethyloxosulfonium methylide is prepared in situ by mixing trimethylsulfonium or trimethylsulfoxonium halide (chloride, bromide or iodide) with a molar excess (molar ratio greater than 1:1) of a strong base in the solvent system. The acetyl compound (Formula V) dissolved in a solvent is then added.

Trimethylsulfonium halides are known compounds and can be prepared as described by H. J. Emeleus et al., J. Chem. Soc. 1126 (1946) and R. Kuhn et al., Ann. 611,117 (1958). For example, dimethylsulfide and methyl halide in a suitable solvent can be quantitatively reacted to form trimethylsulfonium iodide which separates as a solid cake. After a suitable time, for example, 24 hours, it can be collected, crystallized from ethanol and washed with ether.

It can also be prepared in situ; methyl halide can be added to dimethylsulfide in a suitable solvent such as dimethylsulfoxide, and the mixture stirred at 15° to 20°C for 4 hours. The mixture, cooled to 10° to 15°C, can then be mixed with reactants and solvents according to the above procedure. The preferred halides are the bromide or chloride.

Trimethylsulfoxonium halide is also a known compound and can be prepared by the procedure of R. Kuhn et al., Ann. 611,117 (1958). Diemthylsulfoxide, upon extended refluxing (many days) with a methyl halide such as the chloride, bromide, or iodide forms this reagent. It is used in the same manner as the trimethylsulfonium halide.

As a strong base, alkali metal lower alkoxides such as sodium or potassium methoxide, ethoxide, propoxide, n-butoxide, isobutoxide and t-butoxide (preferably sodium alkoxides) or sodium methylsulfinylmethide can be used. These compounds are all known. The last named compound is formed by reacting powdered sodium hydride with excess dimethylsulfoxide and cooling the reaction mixture.

Any conventional inert organic solvent for the reactants can be used. A particularly advantageous solvent is a mixture of dimethylsulfoxide and tetrahydrofuran in a volume ratio of from 1–10:1.

The reaction can be carried out at a temperature of from 0° to 50°C and preferably from 10° to 15°C until the product is formed, preferably for at least 5 minutes after addition of the ketone of Formula V to the reaction mixture is complete. The reaction (as well as the preparation of the methylating agent) should be carried out under an inert atmosphere such as nitrogen and the like.

The 2-(6'-methoxynaphth-2'-yl)propylene oxide or 2-(5'-halo-6'-methoxynaphth-2'-yl)propylene oxide can be separated, for example, by diluting the reaction mixture with water and filtering the precipitated propylene oxide from the mixture. It is then preferably washed and dried in preparation for the next step.

The 2-(6'-methoxynaphth-2'-yl)propylene oxide or 2-(5'-halo-6'-methoxynaphth-2'-yl)propylene oxide (Formula VI) can be converted to the 2-(6'-methoxynaphth-2'-yl)propionaldehyde or 2-(5'-halo-6'-methoxynaphth-2'-yl)propionaldehyde (Formula VII) by several procedures, all of which are indicated by the terms "converting". The propylene oxide can be converted to the aldehyde by heating in the absence of a catalyst at a temperature sufficient to effect conversion to the propionaldehyde, that is above 220°C, either with or without an inert organic solvent. The propylene oxide, when heated (melted without solvent) at a temperature sufficient to effect the conversion (above 120°C and preferably from 120° to 140°C) in the presence of a Lewis acid forms the aldehyde. In an inert organic solvent system in the presence of a Lewis acid, lower temperatures are effective; for example, the aldehyde is formed at temperatures of from 0° to 30°C, preferably from 5° to 10°C. The reactions are conducted in an inert atmosphere such as nitrogen.

Examples of suitable Lewis acids include boron trifluoride etherate, boron trifluoride, boron trichloride, aluminum chloride, zinc chloride, stannic chloride, etc., the preferred Lewis acid being boron trifluoride etherate. A particular suitable inert organic solvent is tetrahydrofuran.

The product 2-(6'-methoxynaphth-2'-yl)propionaldehyde or 2-(5'-halo-6'-methoxynaphth-2'-yl)propionaldehyde can be separated from the reaction mixture by conventional techniques. Separation is unnecessary, however, since the reaction mixture can be concentrated to a form usable in the next process step by distillation under reduced pressure, preferably after adding a base such as pyridine.

The 2-(6'-methoxynaphth-2'-yl)propionaldehyde or 2-(5'-halo-6'-methoxynaphth-2'-yl)propionaldehyde (Formula VII) can then be reacted with hydroxylamine hydrochloride in an inert solvent to form 2-(6'-methoxynaphth-2'-yl)propionaldoxime or 2-(5'-halo-6'-methoxynaphth-2'-yl)propionaldoxime (Formula VIII) according to one process of this invention. The hydroxylamine hydrochloride is a known reagent. Preferably the reaction medium contains a basic catalyst. A preferred solvent system is a mixture of water and pyridine. The hydroxylamine hydrochloride can be added to the reaction mixture as an aqueous solution. At least a slight molar excess of hydroxylamine hydrochloride should be used.

The reaction can be carried out at a temperature of from 20° to 100°C, the lower temperatures being preferred to decrease side reactions. Since the reaction is exothermic, temperatures of the reacting mixture may reach 40°C and higher unless cooling is provided. The reaction is continued until the aldoxime product is formed; since the reaction is very rapid, permitting the reaction mixture to stand for longer than a few minutes is not required.

The aldoxime is then separated from the reaction mixture. For example, the reaction mixture can be diluted with water and extracted with an inert organic, water-immiscible solvent such as methylene chloride, other chlorinated or brominated hydrocarbon liquids, and the like. The preferred solvents are chlorinated solvents such as methylene chloride. The extraction solvent phase [containing the 2-(6'-methoxynaphth-2'-yl)propionaldoxime or corresponding 5'-halo compound] can be concentrated in preparation for the next step. The aldoxime can be separated and purified by crystallization, washing and drying. However, separation is not required, the extracted concentrate being entirely satisfactory for the next process step.

The 2-(6'-methoxynaphth-2'-yl)propionaldoxime or 2-(5'-halo-6'-methoxynaphth-2'-yl)propionaldoxime (Formula VIII) is dehydrated by heating at a temperature sufficient to effect dehydration, usually from 100° to 200°C and preferably at about 120°C or above to form the respective 2-(6'-methoxynaphth-2'-yl)propionitrile or 2-(5'-halo-6'-methoxynaphth-2'-yl)propionitrile (Formula XI). When the reaction is carried out without solvent or in an inert neutral organic solvent system, the product propionitrile can be separated and purified by conventional techniques. The propionitrile can then be hydrolyzed to the corresponding acid by standard hydrolysis technique with a strong acid or base.

Preferably the dehydration and hydrolysis is carried out in a single step by heating the oxime at temperatures of 100° to 200°C, preferably at about 120°C or above in a strong alkaline or strong acid medium. For example, the hydrolysis can be conducted in an alcoholic solution of an alkali metal hydroxide to form an alkali metal salt, acidification providing the carboxylic acid.

Suitable alkaline materials for the hydrolysis include sodium hydroxide, potassium hydroxide, and the like, in aqueous solutions of alcohols including methanol, ethanol, propanol, isopropanol, t-butanol, ethylene glycol, methoxyethanol, and the like, the higher boiling alcohols being preferred. Hydrolysis is preferably conducted in a potassium hydroxide solution in aqueous ethylene glycol. For the hydrolysis, the reaction mixture is heated until the salt of the product is formed, preferably at 125°C.

The reaction mixture is then purified and acidified to form the carboxylic acid which can be separated and purified by conventional techniques. The reaction mixture can be poured into water and extracted with methylene chloride, for example, to remove impurities soluble therein; the aqueous layer can then be diluted with acetone, acidified with a suitable acid such as hydrochloric acid, and heated to distill the acetone from the solution, the carboxylic acid precipitating as the acetone is removed to yield 2-(6'-methoxynaphth-2'-yl)propionic acid (Formula XIV) or 2-(5'-halo-6'-methoxynaphth-2'-yl)propionic acid (Formula XII), depending upon the respective propionaldoxime used.

Alternatively, the hydrolysis (or dehydration-hydrolysis) can be conducted in an aqueous solution of a strong mineral acid such as sulfuric acid, hydrochloric acid, phosphoric acid, and the like, preferably also containing a carboxylic acid having from 1–3 carbons, the latter being present in concentrations sufficient to increase the solubility of the aldoxime of Formula VIII or nitrile of Formula XI in the reaction mixture. Heating the aldoxime at 100° to 200°C, preferably at about 120°C or above provides both the dehydration and hydrolysis, yielding the 2-(6'-methoxynaphth-2'-yl)propionic acid (Formula XIV) or 2-(5'-halo-6'-methoxy-naphth-2'-yl)propionic acid (Formula XII) depending upon whether or not the group at the 5'-position is hydrogen or halogen. The product acid can be separated by conventional means.

Alternatively the 2-(6'-methoxynaphth-2'-yl)propionaldehyde or 2-(5'-halo-6'-methoxynaphth-2'-yl)propionaldehyde of Formula VII can be oxidized directly to the 2-(6'-methoxynaphth-2'-yl)propionic acid (Formula XIV) or 2-(5'-halo-6'methoxynaphth-2'-yl)propionic acid (Formula XII), respectively, with a chromic acid solution. This oxidation is carried out in a mixture of acetone and an aqueous solution of chromic acid having a normality of 6 to 10 and preferably about 8, with cooling (reaction temperature of from −20° to 30°C, preferably from −5° to 10°C. The chromic acid solution can be prepared from water, chromium trioxide and sulfuric acid by known procedures. The propionic acid product can be separated by diluting the reaction mixture with water, separating the precipitated solids, and washing and drying them to yield the respective acid.

The presence of the 5'-halo group greatly increases the oxidation yield of the desired propionic acid product over that obtained with the corresponding 5'-hydrogen aldehyde (where Y=H). The increase in yield is at least 20 percent. Therefore, the preferred reaction procedure throughout this process follows the above diagram wherein Y=X, that is a halo group such as a fluoro, chloro, bromo or iodo group.

The 2-(5'-halo-6'-methoxynaphth-2'-yl)propionic acid of Formula XII can be dehalogenated to yield the 2-(6'-methoxynaphth-2'-yl)propionic acid of Formula XIV by any conventional dehalogenation procedure which will not disturb the other portions of the compound. A particularly suitable procedure comprises reacting the 5'-halo compound of Formula XII (Y=X=halo) with a mixture of magnesium methylate and triethylamine in methanol. For example, a mixture of magnesium powder, methanol, and a molar excess of triethylamine are mixed together, and while maintaining this mixture under an inert atmosphere such as nitrogen, the 2-(5'-halo-6'-methoxynaphth-2'-yl)propionic acid in a methanol solution is added thereto. After the reaction is complete, for example after refluxing for one hour, hydrochloric acid can be added to the reaction mixture to dissolve all remaining magnesium. The propionic acid product (Formula XIV) can be separated by conventional procedures. For example, the reaction mixture can be poured into water and extracted with a suitable solvent such as methylene chloride. The organic layer can then be separated, washed with water, and the 2-(6'-methoxynaphth-2'-yl)propionic acid (Formula XIV) can be crystallized therefrom.

The 2-(6'-methoxynaphth-2'-yl)propionic acid and its corresponding 5'-halo acids have an asymmetric carbon and are obtained as a mixture of optical isomers. These isomers can be separated by preparing salts of the acids with an alkaloid or similar resolving agent such as cinchonidine, and separating the products by fractional crystallization, the d-acid salt being the least soluble in methanol. The d-salts are acid cleaved to yield the respective optically specific isomers, that is, d-2-(6'-methoxynaphth-2'-yl)propionic acid or the corresponding d-5'-halo (fluoro, chloro, bromo, or iodo) compounds. Repeating the procedure with an alkaloid which forms a least soluble salt with the respective lacids provides the pure l-2-(6'-methoxynaphth-2'-yl)propionic acid or the corresponding l-5'-halo compounds.

Useful intermediates of this invention for forming 2-(6'-methoxynaphth-2'-yl)propionic acid by the procedures described above include 2-(6'-methoxynaphth-2'-yl)propylene oxide,
2-(5'-chloro-6'-methoxynaphth-2'-yl)propylene oxide,
2-(5'-bromo-6'-methoxynaphth-2'-yl)propylene oxide,
2-(5'-iodo-6'-methoxynaphth-2'-yl)propylene oxide,
2-(5'-fluoro-6'-methoxynaphth-2'-yl)propylene oxide,
2-(6'-methoxynaphth-2'-yl)propionaldoxime,
2-(5'-chloro-6'-methoxynaphth-2'-yl)propionaldoxime,
2-(5'-bromo-6'-methoxynaphth-2'-yl)propionaldoxime,
2-(5'-iodo-6'-methoxynaphth-2'-yl)propionaldoxime,
2-(5'-fluoro-6'-methoxynaphth-2'-yl)propionaldoxime,
2-(6'-methoxynaphth-2'-yl)propionitrile,
2-(5'-chloro-6'-methoxynaphth-2'-yl)propionitrile,
2-(5'-bromo-6'-methoxynaphth-2'-yl)propionitrile,
2-(5'-iodo-6'-methoxynaphth-2'-yl)propionitrile,
2-(5'-fluoro-6'-methoxynaphth-2'-yl)propionitrile,
2-(5'-chloro-6'-methoxynaphth-2'-yl)propionaldehyde,
2-(5'-chloro-6'-methoxynaphth-2'-yl)propionaldehyde,
2-(5'-iodo-6'-methoxynaphth-2'-yl)propionaldehyde, and
2-(5'-fluoro-6'-methoxynaphth-2'-yl)propionaldehyde.

In another alternate procedure of this invention, 6-methoxy-2-acetylnaphthalene or 5-halo-6-methoxy-2-acetylnaphthalene (Formula V) is reacted with diethylaluminum cyanide in an inert solvent to form 2-hydroxy-2-(6'-methoxynaphth-2'-yl)propionitrile or 2-hydroxy-2-(5'-halo-6'-methoxynaphth-2'-yl)propionitrile, respectively, of Formula IX.

Diethylaluminum cyanide is a known reagent which can be made by reacting triethylaluminum with hydrogen cyanide in a hydrocarbon solvent such as benzene.

The reaction with diethylaluminum cyanide is carried out in an anhydrous solvent system, for example with a hydrocarbon solvent such as a mixture of toluene and benzene. The reaction can be carried out at temperatures of from −50° to 30°C. The best yield is obtained at the lower temperatures, such as from −40° to −10°C. The reaction is continued until the product is formed, usually for at least 5 minutes, and preferably for longer than 10 minutes. The time, of course, will depend upon the reaction conditions, the lower temperatures requiring longer reaction times.

The propionitrile is then separated from the reaction mixture. For example, the reaction mixture can be neutralized by mixing it with an aqueous alkali metal hydroxide solution, and the 2-hydroxy-2-(6'-methoxynaphth-2'-yl)propionitrile or corresponding 5'-halo(-bromo, -chloro, -fluoro or -iodo) compound can be extracted from the mixture with a conventional extraction solvent such as a chlorinated hydrocarbon, e.g., methylene chloride or chloroform. The organic layer is purified and evaporated, and the propionitrile crystallized and separated.

The propionitrile of Formula IX is then dehydrated to form the 2-(6'-methoxynaphth-2'-yl)acrylonitrile or 2-(5'-halo-6'-methoxynaphth-2'-yl)acrylonitrile of Formula X. This dehydration can be accomplished with any conventional dehydrating reagent. Examples of suitable reagents are sulfuric acid, formic acid, acetic anhydride, phosphorus oxichloride, potassium bisulfate (potassium hydrogen sulfate), phosphorus pentoxide, activated alumina, anhydrous potassium carbonate, thionyl chloride, aluminum powder and the like.

The preferred dehydrating agent is potassium bisulfate, and a suitable procedure for using this reagent comprises intimately mixing the cyanohydrin of Formula IX with freshly fused and powdered potassium bisulfate, preferably with a small quantity of hydroquinone, and distilling the acrylonitrile of Formula X from the reaction mixture. The acrylonitrile can be recovered by drying and redistilling the original distillate to yield 2-(6'-methoxynaphth-2'-yl)acrylonitrile or 2-(5'-halo-6'-methoxynaphth-2'-yl)acrylonitrile, depending upon whether the parent cyanohydrin has hydrogen or a halo group at the C-5' position. The temperature conditions for the dehydration reaction will depend upon the particular catalyst used and are known in the art. Depending upon the particular catalyst, the reaction temperature can be within the range of from 0° to 200°C, for example. Using potassium bisulfate, reaction temperatures of from 100° to 200°C and preferably from 130° to 180°C are employed. The reaction time will also depend upon the technique used; with potassium bisulfate, the reaction mixture is heated until vapor evolution is complete.

Alternate procedures can be used for deriving the 2-(6'-methoxynaphth-2'-yl)propionic acid of Formula XIV from the 2-(6'-methoxynaphth-2'-yl)acrylonitrile or 2-(5'-halo-6'-methoxynaphth-2'-yl)acrylonitrile of Formula X. In one procedure, the acrylonitrile of Formula X is first hydrogenated to form the 2-(6'-methoxynaphth-2'-yl)propionitrile of Formula X which is then hydrolyzed to form the propionic acid of Formula XIV.

Catalyic hydrogenation is carried out in an inert solvent using conventional catalysts and procedures. Hydrogenation using platinum oxide catalysts or palladium-on-carbon catalysts has the advantage of room temperature and low pressure operating conditions. Other conventional catalysts such as nickel-on-Kieselguhr or Raney nickel catalysts can be used but they require higher pressures and temperatures of from 25° to 250°C. Simultaneous dehydration and hydrogenation of the cyanohydrin of Formula IX to the propionitrile of Formula XI can also be accomplished with a catalyst such as activated alumina and nickel oxide. In these precedures, the hydrogen is usually bubbled through a solution of the acrylonitrile in an inert organic solvent such as methanol, other lower alcohol, or the like, the solution containing the suspension of the particular catalyst. The product propionitrile is then separated from the reaction mixture. For example, the catalyst can be separated from the reaction mixture, and the product can be then crystallized from the solution. Chloro, bromo and iodo groups at the 5'-position of the naphthalene nucleus are simultaneously replaced with hydrogen using many of the above catalyst systems. In catalytic systems where 5'-halo groups (for example the fluoro group) remain on the hydrogenated product, they can be removed using magnesium methylate and triethylamine in methanol by the procedure described above.

Hydrolysis of the propionitrile of Formula XI can be accomplished using either of the above-described acid or alkaline procedures to form the 2-(6'-methoxynaphth-2'-yl)propionic acid of Formula XIV.

Alternatively, the acrylonitrile of Formula X is first hydrolyzed by one of the above-described procedures to form the 2-(6'-methoxynaphth-2'-yl)acrylic acid or 2-(5'-halo-6'-methoxynaphth-2'-yl)acrylic acid of Formula XIII which is then catalytically hydrogenated to form the product 2-(6'-methoxynaphth-2'-yl)propionic acid of Formula XIv by one of the procedures described above. Dehalogenation of chloro, bromo and iodo groups, as noted above, usually accompanies hydrogenation, but if the halo group remains upon the naphthalene nucleus, it can be removed, for example, by the magnesium methylatetriethylamine procedure described above.

Examples of intermediate compounds of this invention which are useful in the above alternate process include 2-hydroxy-2-(6'-methoxynaphth-2'-yl)propionitrile,
2-hydroxy-2-(5'-chloro-6'-methoxynaphth-2'-yl)propionitrile,
2-hydroxy-2-(5'-bromo-6'-methoxynaphth-2'-yl)propionitrile,
2-hydroxy-2-(5'-iodo-6'-methoxynaphth-2'-yl)propionitrile,
2-hydroxy-2-(5'-fluoro-6'-methoxynaphth-2'-yl)propionitrile,
2-(6'-methoxynaphth-2'-yl)acrylonitrile,
2-(5'-chloro-6'-methoxynaphth-2'-yl)acrylonitrile,
2-(5'-bromo-6'-methoxynaphth-2'-yl)acrylonitrile,
2-(5'-iodo-6'-methoxynaphth-2'-yl)acrylonitrile,
2-(5'-fluoro-6'-methoxynaphth-2'-yl)acrylonitrile,
2-(6'-methoxynaphth-2'-yl)acrylic acid,
2-(5'-chloro-6'-methoxynaphth-2'-yl)acrylic acid,
2-(5'-bromo-6'-methoxynaphth-2'-yl)acrylic acid,
2-(5'-iodo-6'-methoxynaphth-2'-yl)acrylic acid,
2-(5'-fluoro-6'-methoxynaphth-2'-yl)acrylic acid, and 2-(6'-methoxynaphth-2'-yl)propionitrile.

The invention is further illustrated by the following specific but non-limiting examples.

EXAMPLE 1

A stirred solution of 2-methoxynaphthalene (5g.) in acetic acid (100 ml.) is treated dropwise with a solution of 1.1 molar equivalents of bromine in acetic acid (50 ml.). Upon disappearance of the bromine color, wtaer is added. The solid which forms is collected by filtration, washed with water until neutral, recrystallized, rewashed, and dried to yield 1-bromo-2-methoxynaphthalene.

EXAMPLE 2

Repeating the procedure of Example 1 but replacing bromine with 1.1 moles of chlorine (bubbled through the reaction mixture) or 1.1 moles of iodine (in 50 ml. of acetic acid) yields 1-chloro-2-methoxynaphthalene or 1-iodo-2-methoxynaphthalene, respectively.

EXAMPLE 3

2-hydroxynaphthalene (1 g.) is dissolved in boiling acetic acid (30 ml.), and when the solution temperature reaches 45'C, a molecular equivalent amount of concentrated nitric acid is slowly added. After standing overnight at room temperature, the reaction mixture is mixed with water. The precipitated solids are filtered, washed with water, and purified by chromatography on alumina, to yield 1-nitro-2-hydroxynaphthalene.

1-nitro-2-hydroxynaphthalene (0.5 g.) is methylated with a molar excess of dimethyl sulfate in tetrahydrofuran (50 ml.) and 10% potassium hydroxide solution (50 ml.) over a period of 6 to 8 hours with periodic addition of a 40% potassium hydroxide solution (32 ml.) to maintain basicity of the reaction mixture. The 1-nitro-2-methoxynaphthalene product is separated from the reaction mixture, washed and dried.

1-nitro-2-methoxynaphthalene (1 g.) is hydrogenated in absolute ethanol (200 ml.) over Raney nickel catalyst (1 g.) at 25°C and an initial pressure of 40 psi until the theoretical amount of hydrogen is absorbed. The catalyst is removed, the filtrate concentrated to dryness under vacuum, and the residue recrystallized from methanol to yield 1-amino-2-methoxynaphthalene.

A suspension of 1-amino-2-methoxynaphthalene (1 g.) in a mixture of tetrahydrofuran (50 ml.), dioxane (10 ml) and 48% aqueous fluoroboric acid (12.5 ml.) is chilled to 0°C. A solution of sodium nitrate (6.2 g.) in cold water (20 ml.) is added dropwise over 5 minutes to the vigorously stirred mixture while maintaining the temperature at 0° to 10°c. The slurry is stirred for one hour at 0°C and diluted with cold water (650 ml.), precipitating the 1-diazonium fluoroborate of 2-methoxynaphthalene. The precipitate is separated, washed with ether and dried.

A mixture of the diazonium fluoroborate (1 g.) and copper powder (1g.) is spread in a thin layer in a sublimation apparatus and decomposed under vacuum (0.2 mm.) by increasing the oil bath temperature slowly to 170°C over a period of 6 hours. The solid material which had sublimed onto the sides of the still is collected, dissolved in chloroform, filtered, dried, and chromatographed on acid-washed alumina, eluting with benzene to yield 1-fluoro-2-methoxynaphthalene.

EXAMPLE 4

Repeating the procedures of Examples 1 and 2 but replacing 2-methoxynaphthalene with 2-hydroxynaphthalene yields 1-bromo-2-hydroxynaphthalene, 1-chloro-2-hydroxynaphthalene and 1-iodo-2-hydroxynaphthalene, respectively.

EXAMPLE 5

In 15 N sodium hydroxide (100 ml.), 1-chloro-2-hydroxynaphthalene is dissolved, and the solution is filtered and cooled. Dimethyl sulfate (10 ml.) is added to the solution, and the product precipitates from the reaction mixture after a few minutes. The solids are broken up and washed with 1 N sodium hydroxide (100 ml.). The solids are dried azeotropically with benzene followed by distillation to yield 1-chloro-2-methoxynaphthalene.

Repeating this procedure with 1-bromo-2-hydroxynaphthalene or 1-iodo-2-hydroxynaphthalene yields 1-bromo-2-methoxynaphthalene or 1-iodo-2-methoxynaphthalene, respectively.

EXAMPLE 6

By the following procedure, 6-methoxy-2-acetyl-naphthalene was produced. Nitrobenzene (14,000 ml.) and β-naphthol methyl ether (2000 g.) were mixed under nitrogen and cooled to 0° to 5°C. To this solution was added aluminum trichloride (2600 g.) in nitrobenzene (20,000 ml.) precooled to 0° to 5°C. Acetyl chloride (1300 g.) was added to this mixture over a period of 30 to 40 minutes while maintaining the temperature below 25°C. After addition of the acetyl chloride was complete, the mixture was heated to 35°C and maintained at that temperature for 10 hours.

The reaction mixture was repeatedly washed with water containing hydrochloric acid to remove organic impurities from the nitrobenzene layer, and the nitrobenzene layer was concentrated under vacuum to a heavy syrup. The 6-methoxy-2-acetylnaphthalene product was precipitated by adding methanol and then water, filtered, washed, dried, and crystallized from cyclohexane.

Repeating this procedure but replacing the nitrobenzene with dichloromethylene and replacing the β-naphthol methyl ether with 1-bromo-2-methoxynaphthalene, 1- chloro-2-methoxynaphthalene, and 1-fluoro-2-methoxynaphthalene — 5-bromo-6-methoxy-2-acetylnaphthalene, 5-chloro-6-methoxy-2-acetylnaphthalene, and 5-fluoro-6-methoxy-2-acetylnaphthalene, respectively, were produced. A higher yield was obtained starting with the halo compounds, and less extensive processing was required to obtain a product having high purity.

EXAMPLE 7

A mixture of dimethyl sulfoxide (4800 ml.) and tetrahydrofuran (400 ml.) was purged with nitrogen and cooled to 10° to 15°C. To this mixture was added sodium methoxide (500 g.) and trimethylsulfonium iodide (1300 g.). While maintaining the temperature of the mixture at 10° to 15°C, a solution of 6-methoxy-2-acetylnaphthalene (100 g.) in a mixture of dimethyl sulfoxide (2400 ml.) and tetra-hydrofuran (920 ml.) was added over a period of 30 minutes. After maintaining the temperature of the mixture at from 10° to 15°C for another 15 minutes, the reaction mixture was diluted to a total volume of 50,000 ml. with cool water and filtered, and the filter cake washed with water until the washings were neutral. The product 2-(6'-methoxynaphth-2'-yl) propylene oxide was dried at 50°C.

Repeating the procedure but replacing 6-methoxy-2-acetylnaphthalene with 5-bromo-6-methoxy-2-acetylnaphthalene, 5-chloro-6-methoxy-2-acetylnaphthalene and 5-fluoro-6-methoxy-2-acetylnaphthalene — 2-(5'-bromo-6'-methoxynaphth2'-yl)propylene oxide, 2-(5'-chloro-6'-methoxynaphty-2'-yl)-propylene oxide, and 2-(5'-fluoro-6'-methoxynaphth-2'-yl)-propylene oxide, respectively, were obtained.

The trimethylsulfonium iodide used in this example was prepared by slowly adding dimethyl sulfide (2000 g.) to methyl iodide (4660 g.) while cooling in an ice bath. The mixture was left at 20°C overnight, and the solid reaction cake was recrystallized from hot water, dried at 15°C, and stored in a desiccator until used.

EXAMPLE 8

A mixture of tetrahydrofuran (7000 ml.) and 2-(6'-methoxynaphth-2'-yl)propylene oxide (1060 g.) was purged with nitrogen and cooled to 5° to 10°C. During a period of 15 minutes, a solution of boron trifluoride etherate (4 ml.) in tetrahydrofuran (1200 ml.) was added with stirring to the mixture. After the addition was complete, the mixture was stirred for 30 minutes at 5° to 10°C. Pyridine (8 ml.) was added to the reaction mixture, and the resultant mixture was concentrated to 2000 ml. by distillation under reduced pressure. This concentrate contained 2-(6'-methoxynaphth2'-yl)propionaldehyde.

Repeating this procedure but replacing the 2-(6'-methoxynaphth-2'-yl)propylene oxide with 2-(5'-bromo-6'-methoxynaphth-2'-yl)propylene oxide, 2-(5'-chloro-6'-methoxynaphth-2'-yl)propylene oxide, and 2-(5'-fluoro-6'methoxynaphth-2'-yl)propylene oxide — 2-(5'-bromo-6'-methoxynaphth2'-yl)propionaldehyde, 2-(5'-chloro-6'-methoxynaphth-2'-yl)propionaldehyde, and 2-(5'-fluoro-6'-methoxynaphth-2'-yl)propionaldehyde, respectively, are obtained.

EXAMPLE 9

The residue containing 2-(6'-methoxynaphth-2'-yl)propionaldehyde from the procedure of Example 8 was used as produced. To the residue was added pyridine (6500 ml.) and distillation was continued at reduced pressure until the liquid temperature began to rise drastically, indicating the absence of residual tetrahydrofuran. To this was added a solution of hydroxylamine hydrochloride (400 g.) in water (800 ml.), and the mixture was heated in a stirred bath for 15 minutes. The mixture was then cooled, and water (5000 ml.) and methylene chloride (4000 ml.) were added. The mixture was stirred vigorously, and the phases were permitted to separate. The lower organic phase was separated, and the aqueous phase was extracted with methylene chloride. The organic phases containing the 2-(6'-methoxynaphth-2'-yl)propionaldoxime were concentrated to 1500 to 2000 ml. by distillation, first at atmospheric pressure and then under vacuum.

Repeating the above procedure but replacing the 2-(6'-methoxynaphth-2'-yl)propionaldehyde with 2-(5'-bromo6'-methoxynaphth-2'-yl)propionaldehyde, 2-(5'-chloro-6'-methoxynaphth-2'-yl)propionaldehyde, and 2-(5'-fluoro-6'-methoxynaphth-2'-yl)propionaldehyde — 2-(5'-bromo-6'-methoxynaphth-2'-yl)propionaldoxime, 2-(5'-chloro-6'-methoxynaphth-2'-yl)propionaldoxime, and 2-(5'-fluoro-6'-methoxynaphth-2'-yl)propionaldoxime, respectively, are obtained in a concentrated solution.

EXAMPLE 10

Each of the crude residues from the procedure of Example 9 was used in the form produced. To each of these residues was added ethylene glycol (7200 ml.) and a solution of potassium hydroxide (100 g.) in water (100 ml.). With gentle stirring, the mixtures were heated to a temperature of about 125°C and maintained at this temperature for 7 hours. The reaction mixtures each were cooled and poured into water (60,000 ml.), and each of the mixtures was extracted with methylene chloride, the extracts being discarded.

The aqueous layers, diluted with acetone (20,000 ml.) were warmed to 45° to 50°C, and the warmed mixtures were slowly acidified with concentrated hydrochloric acid (750 ml.). The acetone was largely removed by distillation under vacuum, and the resultant suspensions were cooled to 15°C, filtered and washed with water. The damp cakes of 2-(6'-methoxynaphth-2'-yl)propionic acid, 2-(5'-bromo-6'-methoxynaphth2'-yl)propionic acid, 2-(5'-chloro-6'-methoxynaphth-2'-yl)propionic acid, and 2-(5'-fluoro-6'-methoxynaphth-2'-yl)propionic acid, respectively, were redissolved in acetone, treated with charcoal, filtered, concentrated, and reprecipitated with water. The filtered materials were washed with water and dried. The products were mixtures of d- and l- isomers of the respective acids.

EXAMPLE 11

To a magnetically stirred solution of triethylaluminum (15.7 g.) in benzene (40 ml.) is added slowly while cooling with ice a solution of hydrogen cyanide (3.7 g.) in benzene (35 ml.). The benzene is evaporated after the reaction is complete (when ethane evolution ceases), and the residue is distilled to provide diethylaluminum cyanide (14.1 g.), a highly viscous oil.

EXAMPLE 12

One mole of 6-methoxy-2-acetylnaphthalene is added to a mixture of anhydrous benzene (32 ml.) and anhydrous toluene (19 ml.), and the solution is cooled to −25°C. To this is added 2.3 moles of diethylaluminum cyanide prepared by the procedure of Example 11. After 30 minutes, the reaction mixture is poured into a stirred mixture of sodium hydroxide (20 g.) and water (500 ml.), and this mixture is extracted with chloroform. The organic layer is purified and evaporated, and the residue is recrystallized from chloroform. The product is 2-hydroxy-2-(6'-methoxynaphth-2'-yl)propionitrile.

Repeating the procedure but replacing the 6-methoxy-2-acetylnaphthalene with 5-bromo-6-methoxy-2-acetylnaphthalene, 5-chloro-6-methoxy-2-acetylnaphthalene, and 5-fluoro-6-methoxy-2-acetylnaphthalene — 2-hydroxy-2-(5'-bromo-6'-methoxynaphth-2'-yl)propionitrile, 2-hydroxy-2-(5'-chloro-6'-methoxynaphth-2'-yl)propionitrile, and 2-hydroxy-2-(5'-fluoro-6'-methoxynaphth-2'-yl)propionitrile, respectively, are obtained.

EXAMPLE 13

An intimate mixture of 2-hydroxy-2-(6'-methoxynaphth-2'-yl)propionitrile (30 g.), freshly fused and powdered potassium bisulfate (5 g.) and hydroquinone (0.3 g.) is added to a flask and heated under a pressure of 21 to 30 mm. in a oil-bath at 155° to 160°C. The vapor is condensed, and to the distillate is added a little hydroquinone and ether. The water is separated, the ether is dried, and the mixture is distilled to provide 2-(6'-methoxynaphth-2'-yl)acrylonitrile.

Repeating this procedure but replacing 2-hydroxy-2-(6'-methoxynaphth-2'-yl)propionitrile with 2-hydroxy-2-(5'-bromo-6'-methoxynaphth-2'-yl)propionitrile, 2-hydroxy-2-(5'-chloro-6'-methoxynaphth-2'-yl)propionitrile, and 2-hydroxy-2-(5'-fluoro-6'-methoxynaphth-2'-yl)propionitrile — 2-(5'-bromo-6'-methoxynaphth-2'-yl)acrylonitrile, 2-(5'-chloro-6'-methoxynaphth-2'-yl)acrylonitrile, and 2-(5'-fluoro-6'-methoxynaphth-2'-yl)acrylonitrile, respectively, are obtained.

EXAMPLE 14

A quantity of 2-(6'-methoxynaphth-2'-yl)acrylonitrile produced by the procedure of Example 13 (100 g.) is added to a mixture of ethylene glycol (700 ml.) and a solution of potassium hydroxide (100 g.) in water (100 ml.). With gentle stirring, the mixture is heated to a temperature of about 125°C and maintained at this temperature for 7 hours. The reaction mixture is cooled and poured into water (6000 ml.), and the mixture is extracted with methylene chloride, the extracts being discarded.

The aqueous layer, diluted with acetone (2000 ml.), is warmed to 45° to 50°C, and the warmed mixture is slowly acidified with concentrated hydrochloric acid (75 ml.). The acetone is largely removed by vacuum distillation, and the resultant suspension is cooled to 15°C, filtered and washed with water. The damp cake of 2-(6'-methoxy-naphth-2'-yl)acrylic acid is redissolved in acetone, treated with charcoal, filtered, concentrated and reprecipitated with water. The filtered materials were washed with water and dried.

Repeating this procedure but replacing the 2-(6'-methoxynaphth-2'-yl)acrylonitrile with 2-(5'-bromo-6'-methoxynaphth-2'-yl)acrylonitrile, 2-(5'-chloro-6'-methoxynaphth-2'-yl)acrylonitrile, and 2-(5'-fluoro-6'-methoxynaphth-2'-yl)acrylonitrile — 2-(5'-bromo-6'-methoxynaphth-2'-yl)acrylic acid, 2-(5'-chloro-6'-methoxynaphth-2'-yl)acrylic acid, and 2-(5'-fluoro-6'-methoxynaphth-2'-yl)acrylic acid, respectively are obtained.

EXAMPLE 15

Hydrogen is bubbled through a suspension of 0.5 g. of 5% palladium-on-carbon catalyst in 50 ml. of methanol for 30 minutes. A solution of 2 g. of 2-(6'-methoxynaphth-2'-yl)acrylic acid in 200 ml. of methanol is added and hydrogenated with agitation until the uptake of hydrogen has ceased. The catalyst is removed by filtration, and the solution is evaporated to yield dl-2-(6'-methoxynaphth-2'-yl)propionic acid which is recrystallized from methylene chloride:hexane for further purification.

Repeating the procedure with 2-(5'-bromo-6'-methoxynaphth-2'-yl)acrylic acid and 2-(5'-chloro-6'-methoxynaphth-2'-yl)acrylic acid — dl-2-(6'-methoxynaphth-2'-yl)-propionic acid is obtained. Repeating the procedure with 2-(5'-fluoro-6'-methoxynaphth-2'-yl)acrylic acid yields 2-(5'-fluoro-6'-methoxynaphth-2'-yl)propionic acid.

EXAMPLE 16

Following the hydrogenation procedure of Example 15 but replacing the 2-(6'-methoxynaphth-2'-yl)acrylic acid with 2-(6'-methoxynaphth-2'-yl)acrylonitrile, 2-(5'-bromo-6'-methoxynaphth-2'-yl)acrylonitrile and 2-(5'-chloro-6'2'-yl)acrylonitrile — 2-(6'-methoxynaphth-2'-yl)propionitrile is obtained in each instance. Repeating the procedure with 2-(5'-fluoro-6'-methoxynaphtha-2'-yl)-acrylonitrile yields 2-(5'-fluoro-6'-methoxynaphth-2'-yl)propionitrile.

EXAMPLE 17

Following the hydrolysis procedure of Example 14 but replacing 2-(6'-methoxynaphth-2-yl)acrylonitrile with 2-(6'-methoxynaphth-2'-yl)propionitrile or 2-(5'-fluoro-6'-methoxynaphth-2'-yl)propionitrile — dl-2-(6'-methoxynaphth-2'-yl)propionic acid or 2-(5'-fluoro-6'-methoxynaphth-2'-yl)propionic acid, respectively, is formed.

EXAMPLE 18

A solution of 8 N chromic acid (prepared by mixing 26 g. of chromium trioxide with 23 ml. of concentrated sulfuric acid and diluting with water to 100 ml.) is added, under nitrogen, to a stirred solution of 1 g. of 2-(5'-bromo-6'-methoxynaphth-2'-yl)propionaldehyde in 10 ml. of acetone which has been cooled to 0°C; addition of the chromic acid is continued until the color of the reagent persists in the mixture. The mixture is then stirred for 5 minutes at 0° to 5°C and diluted with water. The solid which forms is collected by filtration, washed with water and dried under vacuum to yield dl-2-(5'-bromo-6'-methoxynaphth-2'-yl)propionic acid.

Repeating the procedure with 2-(5'-chloro-6'-methoxynaphth-2'-yl)propionaldehyde, 2-(5'-fluoro-6'-methoxynaphth-2'-yl)propionaldehyde, and 2-(6'-methoxynaphth-2'-yl)propionaldehyde yields dl-2-(5'-chloro-6'-methoxynaphth-2'-yl)propionic acid, dl-2-(5'-fluoro-6'-methoxynaphth-2'-yl)propionic acid, and dl-2-(6'-methoxynaphth-2'-yl)propionic acid, respectively.

The presence of the 5'-halo group, however, greatly increases the yield of the final product, the respective yields being at least 85 to 95 percent from the 5'-halo compounds in contrast to only 75 to 85 percent from the corresponding unhalogenated aldehyde.

EXAMPLE 19

To a 250 ml. flask equipped with a reflux condenser having a nitrogen bubbler was added magnesium powder (60 g.), anhydrous methanol (50 ml.), and triethylamine (10 g.). The flask was swept with nitrogen, and a nitrogen atmosphere was maintained throughout the reaction period. From a dropping funnel was slowly added dl-2-(5'-bromo-6'-methoxynaphth-2'-yl)propionic acid (0.1 mole) in methanol (15.0 g.). The mixture was heated under reflux for one additional hour after the 2-(5'-bromo-6'-methoxynaphth-2'-yl)propionic acid addition was complete. The cooled mixture was mixed with 6 N hydrochloric acid until no magnesium remained. The mixture was poured into water, methylene chloride was added, and the mixture was shaken. The organic layer was separated, washed with water, and the dl-2-(6'-methoxynaphth-2'-yl)propionic acid produce was crystallized by concentrating the solution and adding hexane.

This procedure, repeated with dl-2-(5'-chloro-6'-methoxynaphth-2'-yl)propionic acid, dl-2-(5'-fluoro-6'-methoxynaphth-2'-yl)propionic acid, and dl-2-(5'-iodo-6'-methoxynaphth-2'-yl)propionic acid also yielded dl-2-(6'-methoxynaphth-2'-yl)propionic acid in each instance.

EXAMPLE 20

In separating the mixture of d- and l- isomers formed by the procedure of Examples 10, 15, 17, and 18, dl-2-(6'-methoxynaphth-2'-yl)propionic acid was added to a methanol solution of cinchonidine; and the cinchonidine salt of the d-acid was crystallized from the solution; this salt was recrystallized from a solution of acetone and methanol and then recrystallized from a solution of pyridine and isopropanol, the product was hydrolyzed with hydrochloric acid and extracted with ethyl acetate. The extract was mixed with isopropanol, and the mixture was distilled to remove ethyl acetate and precipitate the product. The precipitate was washed with cool isopropanol and dried to provide d-2-(6'-methoxynaphth-2'-yl)propionic acid having a melting point of 155.3°C and an optical rotation of $[a]D=+65.5°$ (C=1.0 in $CHCl_3$).

Repeating this procedure with dl-2-(6'-methoxynaphth-2'-yl)propionic acids having a halo group at position C-5' (fluoro, chloro, bromo or iodo), the respective d-5'-halo compound is obtained, e.g. d-2-(5'-fluoro-6'-methoxynaphth-2'-yl)propionic acid, d-2-(5'-chloro-6'-methoxynaphth-2'-yl)propionic acid, d-2-(5'-bromo-6'-methoxynaphth-2'-yl)propionic acid, and d-2-(5'-iodo-6'-methoxynaphth-2'-yl)propionic acid.

I claim:
1. A 2-(6'-methoxynaphth-2'-yl)propionaldoxime having at the C-5' position, hydrogen or a halo group.

* * * * *